US00PP36192P2

(12) United States Plant Patent
Hansen

(10) Patent No.: US PP36,192 P2
(45) Date of Patent: Oct. 8, 2024

(54) ***X MANGAVE* PLANT NAMED 'Artistic Liberty'**

(50) Latin Name: **x *Mangave* times *Agave* hybrid**
Varietal Denomination: Artistic Liberty

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 18/445,760

(22) Filed: Jan. 22, 2024

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
CPC ..... A01H 6/00; A01H 5/12
See application file for complete search history.

*Primary Examiner* — Keith O. Robinson

(57) ABSTRACT

A new and unique x *Mangave* plant named 'Artistic Liberty' is characterized by a rounded mound of oblanceolate to rhombic, fleshy, slightly rough foliage that has a chimeral variegation with silver-gray margins, a creamy mint center with light-green frosty streaks, and small wine-colored spots in strong ultraviolet light. Leaves have medium-sized, sharp, firm marginal teeth and firm, sharp, apical spines. The new plant is suitable for the garden or as a potted plant in the garden or home.

1 Drawing Sheet

Botanical classification: x *Mangave* times *Agave* hybrid. Variety denomination: 'Artistic Liberty'.

STATEMENT REGARDING PRIOR DISCLOSURES UNDER 37 CFR 1.77(b)(6)

The new plant has not been sold or offered for sale anywhere in the world and no disclosure of the new plant has been made more than one year prior to the filing of this application.

BACKGROUND OF THE INVENTION

The present invention relates to the new and distinct x *Mangave* hybrid plant, x *Mangave* 'Artistic Liberty' that was discovered on Jan. 10, 2022, by the inventor as a whole plant mutation of 'Sponge Paint' U.S. Plant Pat. No. 32,070 at a wholesale perennial nursery in Zeeland, Michigan, USA. Through trials at the same nursery, the plant was assigned the breeder code 22-sp-MANG-1090. The new plant has been successfully asexually propagated by sterile shoot-tip tissue culture at the same nursery in Zeeland, Michigan since 2024. The asexual tissue culture propagation has been found to produce stable and identical plants that maintain all the unique characteristics of the original plant.

BRIEF SUMMARY OF THE INVENTION

'Artistic Liberty' differs from its parents as well as all other *Manfreda, Agave* and x *Mangave* known to the applicant. The nearest comparison plants are: *Agave ovatifolia* 'Frosted Flecks' (not patented), *Agave ovatifolia* 'Beluga' (not patented), *Agave potatorum* 'Lonkie' (not patented), *Agave isthemensis* 'Ohi Raijin Shiro Nakafu', *Agave simplex* 'Snow Devil' (not patented), and x *Mangave* 'Sweet Tooth' U.S. Plant Pat. No. 34,255.

'Frosted Flecks' has a larger habit, is slower growing, has more lanceolate foliage, the variegation is less distinct and covers the entire leaf. 'Beluga' has a larger habit, is slower growing, the foliage has fewer and larger marginal teeth, and the variegation has broader longitudinal streaks on a whiter center. 'Lonkie' is slower growing, has a more rhombic-shaped leaf, the apical mucro is more orangish, and the marginal teeth are larger with more orangish-brown tips. 'Ohi Raijin Shiro Nakafu' is more compact in habit with fewer leaves, slower growing, the foliage is shorter and the mucro and marginal teeth are larger. 'Snow Devil' is slower growing with fewer leaves, the leaf apices are more acute and the leaves are more lanceolate, with fewer and larger marginal teeth, and the center variegation has broader streaks on a more white background. 'Sweet Tooth' has more lanceolate foliage with larger and more orangish to reddish tan marginal teeth and apical spines.

The parent, 'Sponge Paint', has a slightly larger habit, faster growth rate, and lacks the frosty variegation in the leaf centers on the creamy-mint background.

'Artistic Liberty' is unique from all of the above cultivars and all *Agave*, x *Mangave*, and *Manfreda* known to the inventor by the following combined traits:

1. Rounded mound of oblanceolate to rhombic, sarcous, scaberulous leaves;
2. Leaves have a chimera variegation;
3. Leaf margins develop a silver-gray coloration with small wine-colored spots under strong ultraviolet light exposure;
4. Leaf centers have a creamy mint color with fine, longitudinal, light-green frosty streaks;
5. Leaf margins have medium-sized, sharp, firm, outward to slightly recurved, marginal teeth and a long, firm, sharp apical spine;
6. Slow to moderate growth rate;
7. Foliage is outwardly.

BRIEF DESCRIPTION OF THE DRAWING

The photograph of x *Mangave* 'Artistic Liberty' demonstrates the overall appearance of the new plant including the unique traits as a two-year-old plant grown in Zeeland, Michigan. The colors are as accurate as reasonably possible with color reproductions. Ambient light spectrum, temperature, source, and direction may cause the appearance of minor variations in color.

DETAILED BOTANICAL DESCRIPTION

Figure 1:
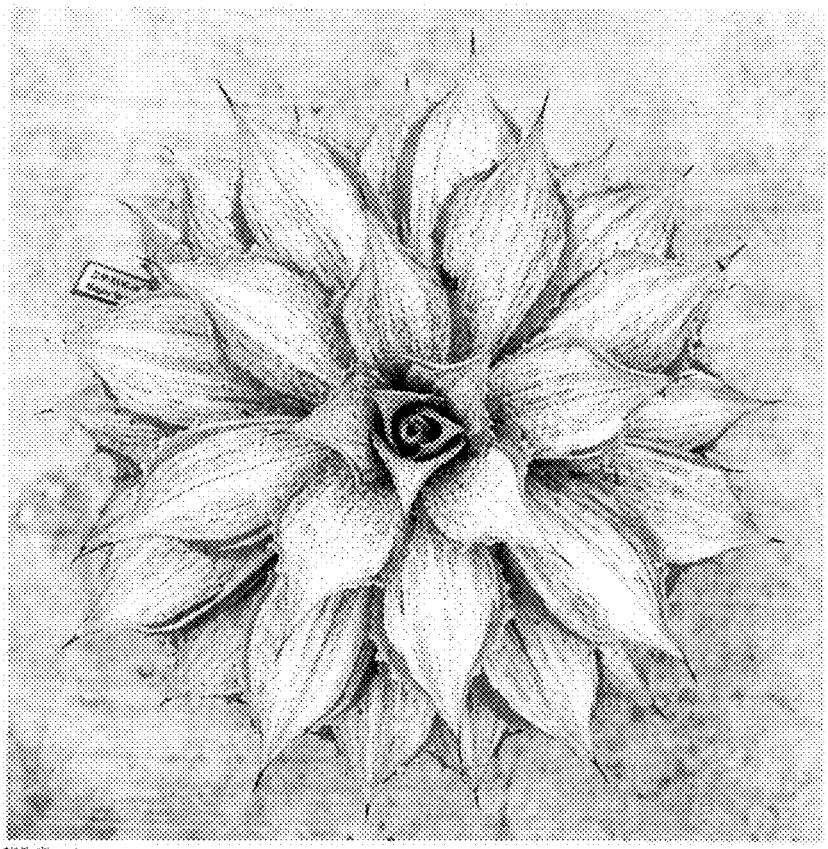
FIG. 1 shows a top view of a greenhouse-grown plant.
Figure 2:
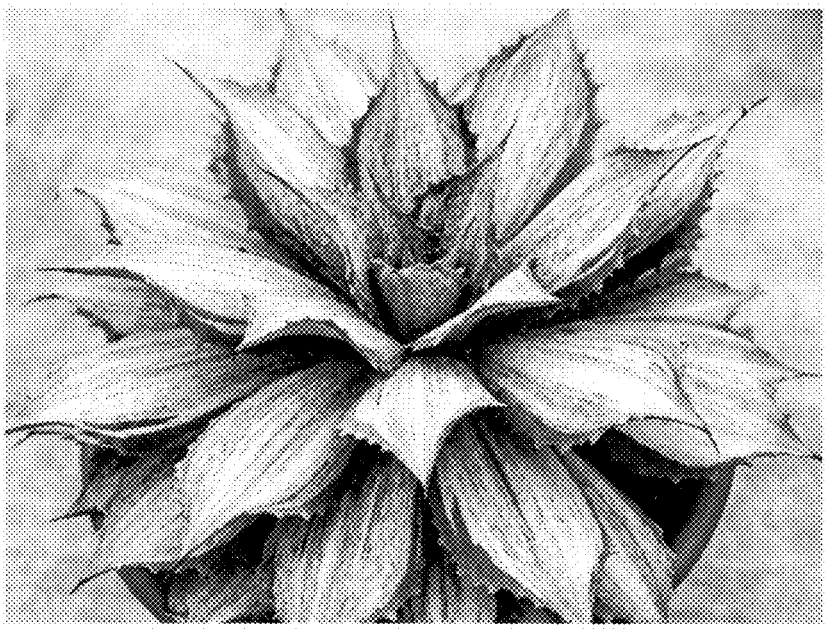
FIG. 2 shows a side view of a greenhouse-grown plant.

The following descriptions and color references are based on the 2015 edition of The Royal Horticultural Society Colour Chart except where common dictionary terms are used. The new plant, x *Mangave* 'Artistic Liberty', has not been observed under all possible environments. Those skilled in the art would recognize that the phenotype leaf color and leaf and plant sizes may vary slightly with maturity and different environmental conditions, such as temperature, light, fertility, moisture, and maturity levels, but without any change in the genotype. The following observations and size descriptions are of a three-year-old plant in a commercial wholesale greenhouse in Zeeland, Michigan with supplemental water and fertilizer as needed.

Parentage: A whole plant mutation of 'Sponge Paint'.

Propagation: By sterile shoot-tip tissue culture.

Time to initiate roots from tissue culture: About 21 days.

Growth rate: Moderate.

Crop time: About 16 to 20 weeks to finish in a 3.8-liter container from a 35 mm tissue culture growing at about 21° C.

Rooting habit: Fleshy, lightly branching, with roots up to 30 cm long.

Root color: Nearest RHS NN155B depending on soil type.

Plant shape and habit: Succulent herbaceous perennial with basal rosettes of leaves radially emerging from the central short stem in a slight upward portion, producing a radially symmetrical, compact, rounded mound.

Plant size: Foliage height about 16 cm tall from the soil line to the top of the leaves and about 34 cm wide at the widest point just about the soil level.

Stem: To about 5 cm across; covered with leaves.

Foliage description: Oblanceolate to rhombic; simple; sessile; bi-laterally symmetrical; with slight coarse wave; sarcous; with solid greyish green margins and centers of creamy white having longitudinal fibers of light green; apex acute with firm terminal spine; base truncate; margins with medium-sized, firm, outwardly to slightly recurved, marginal teeth; glabrous abaxial and adaxial; matte and scaberulous abaxial and adaxial.

Apical spine size: To about 13 mm long and 2 mm wide at the base.

Marginal teeth size: Firm and sharp; about 5 mm long and 7 mm wide at base, average spacing about 6 mm apart.

Leaf size: To about 17 cm long, about 7 cm wide slightly toward the distal side of the middle; center base about 10 mm thick at basal midrib; maculate in high light with adaxial and abaxial reddish spots of variable sizes from 0.5 mm to 3.5 mm across; variegated with bluish-green margin and light minty green center having a random light blush and variably-sized longitudinal threads of bluish-green on both adaxial and abaxial surfaces; threads range from less than 0.5 mm to about 12 mm long and less than 0.05 mm to about 0.5 mm wide.

Foliage fragrance: None observed;

Leaf number: About 60 per plant;

Mature and emerging leaf blade color:

*Adaxial* (*young and low light*).—Margin between RHS 189A and RHS 189B; center nearest RHS 155C with threads between RHS 189B and RHS N138B.

*Abaxial* (*young and low light*).—Margin between RHS 189A and RHS 189B; center nearest RHS NN155B with threads of nearest RHS N138B.

*Adaxial* (*mature and high light*).—Margin between RHS 189A and RHS 189B small reddish spots nearest RHS 187A; center nearest RHS 155C with threads between RHS 189B and RHS N138B and small reddish spots between RHS 186B and RHS 186C.

*Abaxial* (*mature and high light*).—Margin between RHS 189A and RHS 189B small reddish spots nearest RHS 187A; center nearest RHS 155C with threads nearest RHS N138B; and small reddish spots between RHS 186B and RHS 186C.

*Teeth*.—Adaxial between RHS 189A and RHS 189B in the proximal 4 mm and the distal 1 mm between RHS 200A and RHS 200B of mature leaves, and of emerging leaves nearest RHS 200D.

*Terminal spine*.—On young developing leaves between RHS 166A and RHS 166B, on mature leaves nearest RHS 200B.

Petiole: Leaves sessile;

Veins: Parallel; not distinct abaxial or adaxial;

Flower description: Not yet observed;

Fruit and seed: Not observed;

Disease resistance: x *Mangave* 'Artistic Liberty' has not been observed to be resistant to diseases beyond that which is normal for x *Mangave, Agave,* or *Manfreda*. The new plant is xeromorphic and survives well with minimal water once established. The new plant is estimated to be hardy at least from USDA zone 9. The full extent of winter hardiness has not been tested.

It is claimed:

1. A new and distinct cultivar of ornamental x *Mangave* plant named 'Artistic Liberty' as herein described and illustrated.

* * * * *